US007795281B2

(12) United States Patent
Kobayashi et al.

(10) Patent No.: US 7,795,281 B2
(45) Date of Patent: Sep. 14, 2010

(54) OPTICALLY ACTIVE DIHYDROPYRIDINE DERIVATIVE

(75) Inventors: Takashi Kobayashi, Ube (JP); Toshio Sada, Tokyo (JP)

(73) Assignees: Daiichi Sankyo Company, Limited, Tokyo (JP); Ube Industries, Ltd., Ube-Shi, Yamaguchi (JP)

( * ) Notice: Subject to any disclaimer, the term of this patent is extended or adjusted under 35 U.S.C. 154(b) by 0 days.

(21) Appl. No.: 12/214,940

(22) Filed: Jun. 24, 2008

(65) Prior Publication Data

US 2008/0287411 A1    Nov. 20, 2008

Related U.S. Application Data

(63) Continuation of application No. 11/155,844, filed on Jun. 17, 2005, now abandoned, which is a continuation-in-part of application No. PCT/JP03/16616, filed on Dec. 24, 2003.

(30) Foreign Application Priority Data

Dec. 24, 2002  (JP) ............................. 2002-371901

(51) Int. Cl.
*A61K 31/4427* (2006.01)
*C07D 401/12* (2006.01)
(52) U.S. Cl. .................................. 514/340; 546/268.1
(58) Field of Classification Search ................. 514/340; 546/268.1
See application file for complete search history.

(56) References Cited

U.S. PATENT DOCUMENTS 4,772,596 A    9/1988    Koike et al.

FOREIGN PATENT DOCUMENTS

| EP | 266922 A1 | 5/1988 |
|---|---|---|
| JP | HEI 3-31715 A | 2/1991 |
| JP | 11-116570 A | 4/1999 |
| WO | WO 01/76598 A1 | 10/2001 |
| WO | WO 02/09761 A2 | 2/2002 |

OTHER PUBLICATIONS

Masaaki Miyamoto, "Shinki Dihydropyridine-kei Calcium Kikkoyaku Azelnidipine no Ippan Yakuri Sayo", Basic Pharmacology & Therapeutics, 1997, vol. 25, Supplement, 163 (S-1127)-161(S-1145).
Toshio Sada, "Antiatherosclerotic Effects of Azelnidipine, a Long-acting and lipophilic Ca Channel Blocker, in Cholesterol-fed Rabbits", Basic Pharmacology & Therapeutics, Sep. 20, 2002, vol. 30, No. 9, 721-728.
Toshio Sada, "Pharmacological Properties of Azelnidipine, a Long-acting Calcium Channel Blocker with High-affinity for Vascular Tissues (Part 1),", Basic Pharmacology & Therapeutics, Sep. 20, 2002, vol. 30, No. 9, 703-709.
Toshio Sada, "Pharmacological Properties of Azelnidipine, a Long-Acting Calcium Channel Blocker with High-Affinity for Vascular Tissues (Part 2)", Basic Pharmacology & Therapeutics, Sep. 20, 2002, vol. 30, No. 9, 711-720.
Kumi Satoh, "Effects of Azelnidipine, a Dihydropyridine Calcium Antagonist, on Myocarthal Stunning in Dogs," Japanese Journal of Pharmacology, 1998, vol. 76, 369-376.
Mikio Arita, "A New Ca-Antagonist, Azelnidipine Reduced Blood Pressure During Exercise Without Augmentation of Sympathetic Nervous System in Essential Hypertension: A Randomized, Double-Blind, Placebo-Controlled Trial," Journal of Cardiovascular Pharmacology, 1999, vol. 33, No. 2, 186-192.
Kiyoshi Oizumi, "Antihypertensive Effects of CS-905, a Novel Dihydropyridine Ca++ Channel Blocker, Japanese Journal of Pharmacology," 1989, vol. 51, No. 1, 57-64.
Kiyoshi Oizumi, "Antihypertensive Effects of CS-905, a Novel Dihydropyridine Calcium Blocker, in Conscious Hypertensive Dogs," Japanese Journal of Pharmacology, 1990, vol. 53, No. 2, 264-266.
English translation of International Preliminary Examination Report Form PCT/IPEA/409 in International Application No. PCT/JP02003/016616, Jun. 17, 2005.

*Primary Examiner*—Charanjit S Aulakh
(74) *Attorney, Agent, or Firm*—Frishauf, Holtz, Goodman & Chick, P.C.

(57) ABSTRACT

The optically active compound (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester or a pharmacologically acceptable salt thereof, and a method using the compound or its salt to treat circulatory diseases.

15 Claims, No Drawings

OPTICALLY ACTIVE DIHYDROPYRIDINE DERIVATIVE

This application is a Continuation application of Ser. No. 11/155,844 filed Jun. 17, 2005, now abandoned which is a continuation-in-part of International Application PCT/JP2003/016616, filed Dec. 24, 2003, which is incorporated herein in its entirety by this reference.

BACKGROUND OF THE INVENTION

The present invention relates to an optically active dihydropyridine derivative, a pharmacologically acceptable salt thereof having superior blood pressure lowering action, cardiac protective action, anti-arteriosclerotic action and kidney disorder ameliorative action, and a therapeutic agent or preventive agent (to delay or prevent the onset) comprising the same for hypertension, heart diseases, arteriosclerosis and kidney disorders.

Since (±)-2-amino-1,4-dihydro-6-methyl-4-(3-nitrophenyl)-3,5-pyridinedicarboxylic acid 3-(1-diphenylmethylazetidin-3-yl) ester 5-isopropyl ester (hereinafter referred to as Compound (I)), a dihydropyridine calcium antagonist, has pharmacological activities such as calcium antagonistic action, antihypertensive action, vascular dilatory action, cardiac protective action, anti-arteriosclerotic action, diuretic action, renal disorder inhibitory action and lipid peroxide formation inhibitory action and it also has a low level of toxicity, it is known to be useful as a pharmaceutical for treating diseases of the circulatory system such as hypertension, angina pectoris and arteriosclerosis (refer to, for example, Japanese Examined Patent Publication (Kokoku) No. Hei 3-31715 (specification of U.S. Pat. No. 4,772,596)).

BRIEF SUMMARY OF THE INVENTION

With the aim of the development of a superior therapeutic or preventive drug for diseases of the circulatory system, the inventors of the present invention conducted extensive research over many years on the pharmacological activity of various dihydropyridine-based calcium antagonists. As a result, it was found that (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester, which is one of the optical isomers of the racemic form, (±)-2-amino-1,4-dihydro-6-methyl-4-(3-nitrophenyl)-3,5-pyridinedicarboxylic acid 3-(1-diphenylmethylazetidin-3-yl) ester 5-isopropyl ester, has particularly superior pharmacological activities such as calcium antagonistic action, antihypertensive action, vascular dilatory action, cardiac protective action, anti-arteriosclerotic action, diuretic action, renal disorder inhibitory action and lipid peroxide formation inhibitory action, and is useful as a preventive agent or therapeutic agent (particularly therapeutic agent) for diseases of the circulatory system such as hypertension, angina pectoris and arteriosclerosis (particularly hypertension), thereby leading to completion of the present invention.

DETAILED DESCRIPTION OF THE INVENTION

The (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester of the present invention is a compound having the chemical structure indicated below.

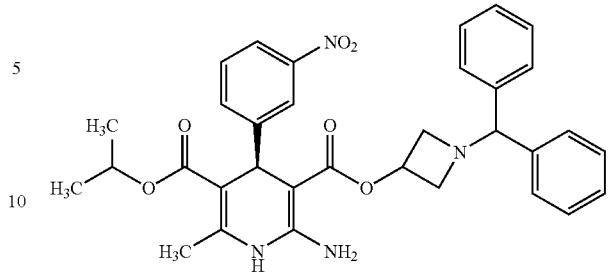

In addition, the active ingredient contained by the preventive agent or therapeutic agent for diseases of the circulatory system such as hypertension and angina pectoris of the present invention is (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester.

The (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester of the present invention may be converted to a salt in accordance with ordinary methods as desired. For example, such a salt can be obtained by treating compound (I) with the corresponding acid for 5 to 30 minutes in a solvent (such as an ether, ester or alcohol and preferably an ether) followed by filtering the precipitated crystals or distilling off the solvent under reduced pressure. Examples of such salts include salts of inorganic acids such as hydrofluorides, hydrochlorides, hydrobromides, hydroiodides, nitrates, perchlorates, sulfates or phosphates, sulfonates such as methanesulfonates, trifluoromethanesulfonates, ethanesulfonates, benzenesulfonates or p-toluenesulfonates, carboxylates such as fumarates, succinates, citrates, tartrates, oxalates or maleates, or salts of amino acids such as glutamates or aspartates.

The (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester of the present invention or a pharmacologically acceptable salt thereof may exist in the form of their respective hydrates, and each of these along with their mixtures are included in the present invention.

The (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester of the present invention can be produced by optically resolving (±)-2-amino-1,4-dihydro-6-methyl-4-(3-nitrophenyl)-3,5-pyridinedicarboxylic acid 3-(1-diphenylmethylazetidin-3-yl) ester 5-isopropyl ester that is produced in accordance with the method described in Japanese Examined Patent Publication (Kokoku) No. Hei 3-31715 (specification of U.S. Pat. No. 4,772,596).

The (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester or a pharmacologically acceptable salt thereof of the present invention exhibits particularly superior pharmacological activities such as calcium antagonistic action, antihypertensive action, vascular dilatory action, cardiac protective action, anti-arteriosclerotic action, diuretic action, renal disorder inhibitory action and lipid peroxide formation inhibitory action, and is useful as a preventive agent or therapeutic agent (particularly therapeutic agent) for diseases of the circulatory system such as hypertension, angina pectoris and arteriosclerosis (particularly hypertension).

In the case where (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester or a pharmacologically acceptable salt of the present invention is used as a preventive agent or therapeutic agent for the above diseases, they can be administered per se orally in the form of a tablet, a capsule, a granule, a powder or a syrup prepared according to a known method using appropriate pharmacologically acceptable additives such as excipients, lubricants, binders, disintegrating agents, emulsifiers, stabilizers, corrigents and diluents or parenterally by an injection or a suppository.

The employable "excipient" can include an organic excipient such as sugar derivatives, e.g., lactose, sucrose, glucose, mannitol or sorbitol; starch derivatives, e.g., corn starch, potato starch, α-starch or dextrin; cellulose derivatives, e.g., crystalline cellulose; gum arabic; dextran; or pullulan; or an inorganic excipient such as silicate derivatives, e.g., light anhydrous silicic acid, synthetic aluminum silicate, calcium silicate or magnesium metasilicate aluminate; phosphates, e.g. calcium hydrogenphosphate; carbonates, e.g., calcium carbonate; or sulfates, e.g., calcium sulfate.

The employable "lubricant" can include stearic acid; metal stearates such as calcium stearate or magnesium stearate; talc; colloidal silica; waxes such as beeswax and spermaceti; boric acid; adipic acid; sulfates such as sodium sulfate; glycol; fumaric acid; sodium benzoate; DL-leucine; lauryl sulfates such as sodium lauryl sulfate and magnesium lauryl sulfate; silicic acids such as anhydrous silicic acid and silicic hydrate; or the above starch derivatives.

The employable "binder" can include hydroxypropyl cellulose, hydroxypropylmethyl cellulose, polyvinylpyrrolidone, Macrogol or a compound similar to the above excipients.

The employable "disintegrating agent" can include cellulose derivatives such as low substituted hydroxypropyl cellulose, carboxymethyl cellulose, calcium carboxymethyl cellulose or internally crosslinked sodium carboxymethyl cellulose; crosslinked polyvinylpyrrolidone; or chemically modified starch/cellulose such as carboxymethyl starch or sodium carboxymethyl starch.

The employable "emulsifier" can include colloidal clays such as bentonite or bee gum; metal hydroxides such as magnesium hydroxide or aluminum hydroxide; anionic surfactants such as sodium laurylsulfate or calcium stearate; cationic surfactants such as benzalconium chloride; or nonionic surfactants such as polyoxyethylene alkyl ether, polyoxyethylene sorbitan fatty acid ester or sucrose fatty acid ester.

The employable "stabilizer" can include parahydroxybenzoates such as methyl paraben or propyl paraben; alcohols such as chlorobutanol, benzyl alcohol or phenylethyl alcohol; benzalconium chloride; phenols such as phenol or cresol; thimerosal; dehydroacetic acid; or sorbic acid.

The employable "corrigent" can include sweeteners such as saccharin sodium or aspartame; sour agents such as citric acid, malic acid or tartaric acid; or perfumes such as menthol, lemon extract or orange extract.

The employable "diluent" can include a compound usually used as a diluent, for example, lactose, mannitol, glucose, sucrose, calcium sulfate, calcium phosphate, hydroxypropyl cellulose, fine crystalline cellulose, water, ethanol, polyethylene glycol, propylene glycol, glycerol, starch, polyvinylpyrrolidone, magnesium metasilicate aluminate or a mixture of them.

The dose of (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester of the present invention or its pharmacologically acceptable salt can be varied depending on the various conditions such as symptoms, age and body weight of the patient. In the case of the oral administration, 0.002 mg/kg (preferably 0.01 mg/kg) as a lower limit and 10 mg/kg (preferably 5 mg/kg) as an upper limit can be administered once to six times per day for an adult warm-blooded mammal (preferably a human adult) in response to the symptoms. In the case of the parenteral administration, 0.0002 mg/kg (preferably 0.001 mg/kg) as a lower limit and 10 mg/kg (preferably 5 mg/kg) as an upper limit can be administered once to six times per day for an adult warm-blooded mammal (preferably a human adult) in response to the symptoms.

In the following, the present invention is further described in detail by indicating Examples, Test Examples and Preparation Examples but the present invention is not limited to them.

EXAMPLES

Example 1

Preparation of (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester (a) Preparation of (±)-2-amino-1,4-dihydro-6-methyl-4-(3-nitrophenyl)-3,5-pyridinedicarboxylic acid 3-(1-diphenylmethylazetidin-3-yl) ester 5-isopropyl ester According to Japanese Examined Patent Publication (Kokoku) No. Hei 3-31715, sodium methoxide (0.27 g) was added to a solution of 2-(3-nitrobenzylidene)acetoacetic acid isopropyl ester (1.39 g) and amidinoacetic acid (1-benzhydryl-3-azetidinyl) ester acetate (1.62 g) in isopropyl alcohol (80 ml) and the mixture was heated under reflux for 4 hours. After the reaction mixture was cooled, insoluble material was removed and the solvent was evaporated under reduced pressure. The thus obtained residue was dissolved in ethyl acetate and the mixture was washed with water, followed by drying over anhydrous sodium sulfate. The solvent was evaporated under reduced pressure and the residue was subjected to silica gel column chromatography (toluene:ethyl acetate=3:1) to obtain pale yellow (±)-2-amino-1,4-dihydro-6-methyl-4-(3-nitrophenyl)-3,5-pyridinedicarboxylic acid 3-(1-diphenylmethylazetidin-3-yl) ester 5-isopropyl ester (2.17 g, 74%).

Melting point: 95-98° C.;

IR spectrum (KBr, $\lambda_{max}$ cm$^{-1}$): 3450, 3310, 1675;

Mass spectrum (CI, m/z)=583 (M$^+$+1); $^1$H NMR (CDCl$_3$) δ ppm: 1.08, 1.26 (6H, 2×d, J=6 Hz), 2.35 (3H, s), 2.63, 3.06, 3.50, 3.62 (4H, 4×t, J=8 Hz), 4.26 (1H, s), 4.9-5.0 (3H, m), 6.04 (1H, br.s), 6.11 (2H, br.s), 7.1-8.2 (14H, m).

(b) Preparation of (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester (R form)

(±)-2-Amino-1,4-dihydro-6-methyl-4-(3-nitrophenyl)-3,5-pyridinedicarboxylic acid 3-(1-diphenylmethylazetidin-3-yl) ester 5-isopropyl ester (racemic form) obtained as above was subjected to high performance liquid chromatography (HPLC) under the following conditions to separate (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester (hereinafter abbreviated as R form) and (S)-2-amino-1,4-dihydro-6-methyl-4-(3-nitrophenyl)-3,5-pyridinedicarboxylic acid 3-(1-diphenylmethylazetidin-3- yl) ester 5-isopropyl ester (hereinafter abbreviated as S form). Regarding the respective separated optical isomers, optical purity was measured under the following analytical conditions.

Conditions of Preparative HPLC
  Column: SUMICHIRAL OA-2000 (15 μm), 5.0 cmϕ×30 cm
  Mobile phase: hexane/1,2-dichloroethane/ethanol (68/29/3) (V/V/V)
  Flow rate: 40 ml/min
  Detector: UV (254 nm)
  Column temperature: 25° C.
  Sample concentration: racemic form 1 g/10 ml of (chloroform: mobile phase (3:1) (V/V)) mixture
  Sample pouring amount: 2 ml Conditions of Analytical HPLC
  Column: SUMICHIRAL OA-2000 (5 μm), 4.6 mmϕ×25 cm
  Mobile phase: hexane/1,2-dichloroethane/ethanol (20/10/1) (V/V)
  Flow rate: 1.0 ml/min
  Detector: UV (254 nm)
  Column temperature: 25° C.

Retention Time Under the Above Analytical Conditions: 9.1 min

Property: Yellow Solid
  $[\alpha]^D_{20}$: −68.4° (c=1.00, ethanol)
  Mass spectrum (CI, m/z): 583 (M$^+$1), 167.
  NMR spectrum (CDCl$_3$, δ): 1.07 (3H, d, J=5.9 Hz), 1.25 (3H, d, J=5.9 Hz), 2.35 (3H, s), 2.67-2.84 (1H, br), 3.13-3.27 (1H, br), 3.57-3.68 (1H, br), 3.68-3.83 (1H, br), 4.32-4.44 (1H, br), 4.86-5.12 (3H, m), 6.08-6.36 (3H, br), 7.12-7.55 (11H, m), 7.60 (1H, d, J=8.1 Hz), 8.04 (11H, d, J=8.1 Hz), 8.17 (1H, s).
  IR spectrum (KBr, $\lambda_{max}$ cm$^{-1}$): 3447, 3319, 1678.

(S)-2-amino-1,4-dihydro-6-methyl-4-(3-nitrophenyl)-3,5-pyridinedicarboxylic acid 3-(1-diphenylmethylazetidin-3-yl) ester 5-isopropyl ester (S form)

Retention Time Under the Above Analytical Conditions: 10.8 min

Property: Yellow Solid
  $[\alpha]^D_{20}$: +68.9° (c=1.00, ethanol) NMR spectrum (CDCl$_3$, δ ppm): 1.07 (3H, d, J=5.9 Hz), 1.25 (3H, d, J=5.9 Hz), 2.36 (3H, s), 2.63-2.77 (1H, br), 3.05-3.24 (1H, br), 3.52-3.64 (1H, br), 3.64-3.78 (1H, br), 4.29-4.41 (1H, br), 4.88-5.09 (3H, m), 6.04-6.29 (3H, br), 7.11-7.49 (11H, m), 7.61 (1H, d, J=7.3 Hz), 8.04 (1H, d, J=8.1 Hz), 8.16 (1H, s).
  IR spectrum (KBr, $\lambda_{max}$ cm$^{-1}$): 3446, 3320, 1678.

Test Example 1

Receptor Binding Experiment Using Porcine Myocardial Microsomes

Porcine myocardial microsomes were used for the source of the L calcium channel, while $^3$H-nitrendipine was used for the ligand of the L calcium channel. The microsomes (0.2 mg protein/ml), $^3$H-nitrendipine (0.1 nM) and test drug (racemic form, R form or S form) were allowed to react at room temperature for 30 minutes in HEPES buffer (50 mM, pH 7.4) followed by measurement of the $^3$H-nitrendipine that bound to the microsome fraction with a liquid scintillation counter. The count in the presence of 10 μM non-labeled nitrendipine (amount of non-specific binding) was then subtracted to determine the amount of specific binding. The relationship between the concentration and inhibition rate of specific binding was approximated to a logistic curve for each test drug to determine IC$_{50}$ (50% inhibitory concentration of specific binding). The Ki value (inhibition constant) for each test drug was then determined from the following formula using the Kd (dissociation constant) of nitrendipine as separately determined from a Scatchard plot:

$$Ki=IC_{50}/(1+[L]/Kd)$$

(wherein [L] is the concentration of $^3$H-nitrendipine). The obtained results (average of two experiments) are shown in Table 1.

TABLE 1

| Compound | IC$_{50}$ (nM) | Ki (nM) |
| --- | --- | --- |
| Racemic form | 3.1 | 2.1 |
| R form | 1.3 | 0.88 |
| S form | 700 | 460 |

The L calcium channel inhibitory activity of the R form was found to be roughly 500 times more potent than that of the S form, and more than twice as potent as that of the racemic form.

Test Example 2

Blood Pressure Lowering Action in Hypertensive Rats

Cannulas for measuring blood pressure and administering drug were inserted into the inguinal artery and inguinal vein, respectively, of male spontaneously hypertensive rats age 25 to 29 weeks followed by intravenous administration of a compound under anesthesia and measurement of blood pressure over time for the course of 120 minutes.

The results of comparing the racemic form (20 μg/kg) and R form (10 μg/kg) are shown in Table 2, while the results of comparing the R form (3 μg/kg, 10 μg/kg) and the S form (1000 μg/kg) in a different series of experiments are shown in Table 3.

TABLE 2

| | Compound Dose | |
| --- | --- | --- |
| (No. of animals) | Racemic form 20 μg/kg (4) | R form 10 μg/kg (5) |
| Change in blood pressure (mmHg) | | |
| 0 minutes | 0 ± 0 | 0 ± 0 |
| 10 minutes | −21 ± 2 | −17 ± 4 |
| 30 minutes | −35 ± 4 | −28 ± 5 |
| 60 minutes | −42 ± 6 | −43 ± 7 |
| 90 minutes | −45 ± 6 | −45 ± 7 |
| 120 minutes | −48 ± 7 | −47 ± 6 |

Mean ± standard error

TABLE 3

| (No. of animals) | Compound Dose | | |
|---|---|---|---|
| | R form 3 µg/kg (3) | R form 10 µg/kg (3) | S form 1000 µg/kg (3) |
| Change in blood pressure (mmHg) | | | |
| 0 minutes | 0 ± 0 | 0 ± 0 | 0 ± 0 |
| 10 minutes | −3 ± 3 | −23 ± 5 | −5 ± 1 |
| 30 minutes | −14 ± 3 | −36 ± 6 | −18 ± 6 |
| 60 minutes | −28 ± 3 | −49 ± 11 | −29 ± 10 |
| 90 minutes | −34 ± 5 | −54 ± 8 | −36 ± 7 |
| 120 minutes | −34 ± 10 | −61 ± 6 | −35 ± 4 |

Mean ± standard error

According to the above results, the R form was found to demonstrate blood pressure lowering activity roughly twice as potent as that of the racemic form and roughly 300 times more potent than that of the S form.

Preparation Example 1

| Capsule | |
|---|---|
| R form | 50.0 mg |
| Lactose | 128.7 |
| Corn starch | 70.0 |
| Magnesium stearate | 1.3 |
| | 250 mg |

The powder of the above formulation was mixed and after the mixture passed through a screen of 60 mesh, the powder was filled in a No. 3 gelatin capsule of 250 mg to make a capsule preparation.

Preparation Example 2

| Tablet | |
|---|---|
| R form | 50.0 mg |
| Lactose | 124.0 |
| Corn starch | 25.0 |
| Magnesium stearate | 1.0 |
| | 200 mg |

The powder of the above formulation was mixed and tablet-making was carried out using a tablet machine to make a tablet of 200 mg per one tablet. Sugar coating can be applied, if necessary, to this tablet.

Since (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester or a pharmacologically acceptable salt of the present invention shows particularly superior pharmacological activities such as a calcium antagonistic action, an antihypertensive action, a vasodilator action, a cardiac protective action, an anti-arteriosclerotic action, a diuretic action, a kidney damage inhibitory action and a lipid peroxide formation inhibitory action and it also has a low level of toxicity, it is useful as a preventive agent to prevent or delay the onset of or therapeutic agent (particularly therapeutic agent) for, circulatory system diseases such as hypertension, angina pectoris and arteriosclerosis (particularly hypertension).

What is claimed is:

1. A compound designated (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester or a pharmacologically acceptable salt thereof, substantially free of the (S) isomer or its salt.

2. The compound of claim 1 designated (R)-2-amino-1,4-dihydro-6-methyl-4-(3-nitrophenyl)-3,5-pyridinedicarboxylic acid 3-(1-diphenylmethylazetidin-3-yl) ester 5-isopropyl ester.

3. A pharmacologically acceptable salt of the compound of claim 1.

4. The salt of claim 3, wherein the salt is a salt of an acid selected from the group consisting of hydrofluorides, hydrochlorides, hydrobromides and hydroiodides.

5. The salt of claim 3, wherein the salt is a nitrate, perchlorate, sulfate, phosphate, sulfonate or carboxylate.

6. The salt of claim 3, wherein the salt is a salt of an amino acid.

7. A composition for treating a circulatory disease which is angina pectoris comprising an effective amount of the compound of claim 1 or a pharmacologically acceptable salt thereof combined with a pharmacologically acceptable additive.

8. A method for treating a circulatory disease which is angina pectoris comprising administering an effective amount of the compound of claim 1 or a pharmacologically acceptable salt thereof to a warm-blooded mammal in need of such treatment.

9. The method of claim 8 wherein the mammal is an adult human.

10. A composition for treating a circulatory disease which is arteriosclerosis, comprising an effective amount of the compound of claim 1 or a pharmacologically acceptable salt thereof combined with a pharmacologically acceptable additive.

11. A method for treating a circulatory disease which is arteriosclerosis, comprising administering an effective amount of the compound of claim 1 or a pharmacologically acceptable salt thereof to a warm-blooded mammal in need of such treatment.

12. The method of claim 11 wherein the mammal is an adult human.

13. A composition for treating a circulatory disease which is hypertension, comprising an effective amount of the compound of claim 1 or a pharmacologically acceptable salt thereof combined with a pharmacologically acceptable additive.

14. A method for treating a circulatory disease which is hypertension, comprising administering an effective amount of the compound of claim 1 or a pharmacologically acceptable salt thereof to a warm-blooded mammal in need of such treatment.

15. The method of claim 14, wherein the mammal is an adult human.

* * * * *